(12) United States Patent
Heo et al.

(10) Patent No.: US 10,507,166 B2
(45) Date of Patent: Dec. 17, 2019

(54) APPARATUS AND METHOD OF MANUFACTURING MULTI-COLUMN MULTI-MEDICINE ORAL DISSOLVING FILM

(71) Applicant: C. L. Pharm, Seoul (KR)

(72) Inventors: Su Hak Heo, Chungcheongnam-do (KR); Gi Hwan Kim, Gyeonggi-do (KR); Kang Mo Sung, Chungcheongnam-do (KR); Seok Hoon Chang, Seoul (KR)

(73) Assignee: C. L. Pharm, Seoul (KR)

( * ) Notice: Subject to any disclaimer, the term of this patent is extended or adjusted under 35 U.S.C. 154(b) by 359 days.

(21) Appl. No.: 15/533,318

(22) PCT Filed: Sep. 3, 2015

(86) PCT No.: PCT/KR2015/009296
§ 371 (c)(1),
(2) Date: Jun. 5, 2017

(87) PCT Pub. No.: WO2016/108392
PCT Pub. Date: Jul. 7, 2016

(65) Prior Publication Data
US 2017/0340520 A1    Nov. 30, 2017

(30) Foreign Application Priority Data
Dec. 31, 2014   (KR) ........................ 10-2014-0194872

(51) Int. Cl.
*A61K 9/00*   (2006.01)
*A61K 9/70*   (2006.01)
(Continued)

(52) U.S. Cl.
CPC ................. *A61J 3/00* (2013.01); *A61J 3/005* (2013.01); *A61K 8/02* (2013.01); *A61K 8/0204* (2013.01);
(Continued)

(58) Field of Classification Search
USPC ..... 53/428, 435, 54, 111 R, 514; 118/16, 20; 424/439; 427/2.31
See application file for complete search history.

(56) References Cited

U.S. PATENT DOCUMENTS 8,936,825 B2 * 1/2015 Myers et al. .......... A61K 31/47
427/2.14
9,149,959 B2 * 10/2015 Bogue .................. A61K 9/0014
(Continued)

FOREIGN PATENT DOCUMENTS

JP   05-124954   5/1993   ............... A61K 9/00
JP   10-201429   8/1998   ............... A23L 1/00
(Continued)

OTHER PUBLICATIONS

Japanese Office Action from corresponding Japanese Application No. 2016-522788 dated Oct. 29, 2017.
(Continued)

*Primary Examiner* — Stephen F. Gerrity
(74) *Attorney, Agent, or Firm* — Harness, Dickey & Pierce, P.L.C.

(57) ABSTRACT

In an apparatus and method of manufacturing a multi-column multi-medicine oral dissolving film according to the present invention, all processes from film feeding, medicine coating, and medicine drying to product packaging are implemented as continuous automation processes, and under the automation processes, different kinds of medicines are coated on a base film in multiple columns in a signal layer by using a plurality of nozzles supplied with the different
(Continued)

kinds of medicines, so that it is possible to improve productivity through the automation processes, to ensure product quality due to efficiency during drying caused by maintaining the thickness of the product, and to provide a convenience in the case of taking various kinds of small-amount medicines at one time or in the case of separately and selectively taking different kinds of medicines.

11 Claims, 7 Drawing Sheets

(51) Int. Cl.
    *A61J 3/00*     (2006.01)
    *A61Q 11/00*     (2006.01)
    *A61K 8/02*     (2006.01)
    *B65D 65/46*     (2006.01)

(52) U.S. Cl.
    CPC .............. *A61K 9/00* (2013.01); *A61K 9/0056* (2013.01); *A61K 9/70* (2013.01); *A61K 9/7007* (2013.01); *A61Q 11/00* (2013.01); *B65D 65/46* (2013.01)

(56) References Cited

U.S. PATENT DOCUMENTS

| | | | | |
|---|---|---|---|---|
| 2002/0116903 | A1* | 8/2002 | Otsu et al. | A45D 40/0087 53/440 |
| 2005/0172578 | A1* | 8/2005 | Ueda et al. | A61K 8/0208 53/435 |
| 2005/0186253 | A1* | 8/2005 | Lee et al. | A61J 3/00 424/439 |
| 2009/0196907 | A1* | 8/2009 | Bunick et al. | A61K 9/0056 424/439 |
| 2009/0304753 | A1* | 12/2009 | Tsabari et al. | A61J 3/071 424/400 |
| 2011/0290694 | A1* | 12/2011 | Fuisz et al. | A61J 3/00 206/459.5 |
| 2012/0263865 | A1* | 10/2012 | Bogue | A61K 9/7007 427/9 |
| 2014/0011893 | A1 | 1/2014 | Stenberg | 514/777 |
| 2014/0105958 | A1* | 4/2014 | Ntoya | A61K 9/0056 424/439 |
| 2014/0113042 | A1* | 4/2014 | Sung et al. | B05B 13/0463 426/303 |
| 2016/0175296 | A1* | 6/2016 | Baer, II et al. | A61K 31/485 514/282 |

FOREIGN PATENT DOCUMENTS

| | | | | |
|---|---|---|---|---|
| JP | 2010-513388 | 4/2010 | ............. | A61K 47/10 |
| KR | 10-2009-0034882 | 4/2009 | ........... | A23L 29/269 |
| KR | 10-1013206 | 2/2011 | ............... | A23L 1/00 |
| KR | 10-2013-0095717 | 8/2013 | ............. | B32B 27/30 |
| KR | 10-1398973 | 6/2014 | ............... | A23L 1/00 |
| WO | 2008/129707 | 10/2008 | ............... | A61K 8/73 |

OTHER PUBLICATIONS

International Search Report from corresponding PCT Application No. PCT/KR2015/009296 dated Dec. 24, 2015 and its English translation.

* cited by examiner

APPARATUS AND METHOD OF MANUFACTURING MULTI-COLUMN MULTI-MEDICINE ORAL DISSOLVING FILM

CROSS-REFRENCE TO RELATED APPLICATIONS

This application is a national phase application of PCT Application No. PCT/KR2015/009296, filed on 3 Sep. 2015, which claims benefit of Korean Patent Application 10-2014-0194872, filed on 31 Dec. 2014. The entire disclosure of the application identified in this paragraph in incorporated herein by references.

FIELD

The present invention relates to an apparatus and method of manufacturing a multi-column multi-medicine oral dissolving film, and more particularly, to an apparatus and method of manufacturing a multi-column multi-medicine oral dissolving film capable of continuously automatically producing and packaging an oral dissolving film for an oral refreshing agent, an oral cleaning agent, or a pharmaceutical product.

BACKGROUND

In general, an oral dissolving film (ODF) refers to a dosage form to be taken and dissolved in the oral cavity such as the tongue, the oral mucosa, or the subglossal. The oral dissolving film includes an edible film manufactured by mixing materials which is soluble in water and is not harmful to a human body with substances which is useful for the human body.

These oral dissolving films are advantageous in that the oral dissolving film can be taken without water and are convenient to carry.

The oral dissolving film (edible film) is usually vulnerable to moisture and is provided in a form of a thin film. The oral dissolving film is cut with appropriate sizes, and each oral dissolving film is sealed and packaged with a wrapping sheet one by one. In the use, the wrapping sheet is cut off and drawn out. Alternatively, the wrapping sheet is drawn out one by one from a dispenser storing the oral dissolving films cut with a certain size. Alternatively, the oral dissolving film is cut off with a certain size and drawn out from a dispenser storing a roll of the oral dissolving film.

Such an oral dissolving film (edible film) is manufactured by coating an edible liquid material on a base film sheet and drying, and the oral dissolving film is wound in a form of a roll to be stored. Alternatively, the oral dissolving film is transferred to a packaging machine. In the packaging machine, the oral dissolving film is slit and cut into individual products, and individual products are inserted into each wrapping member, packaged, and sealed one by one.

However, in the method for manufacturing an oral dissolving film (edible film) in the related art, there are problems as follows. Namely, since the packaging is performed after the slitting and cutting of the film, the number of manufacturing steps is increased. In addition, since the film is stored in a form of a roll, an inventory of semi-finished products is increased, and thus, there are problems such as a decrease of productivity and an increase of costs due to inventory burden. In addition, sanitation management is additionally required.

In view of these problems, Korean Patent No. 10-1013206 discloses an apparatus and method of manufacturing an oral dissolving film capable of simplifying manufacturing facilities and preventing contamination in transfer and storage of the oral dissolving film by manufacturing the oral dissolving film through a method of intermittently coating an edible film prepared by using an intermittent coating apparatus, drying the film, and automatically packaging the film.

However, in the apparatus and method of manufacturing an edible film as described in Korean Patent No. 10-1013206, a product is manufacturing in a form that the edible film is coated with the same medicine in multiple columns in a single layer, there are many inconveniences for users in situations where it is necessary to take various kinds of medicines at the same time.

For example, since a product is manufactured by coating with the same medicine in a single layer and separately packaging, in the case of taking various kinds of small-amount medicines, there is an inconvenience in that the separately packaged medicines need to be unpacked to take one by one.

In order to solve the problems, several proposals have been made on products where an oral dissolving film (edible film) is coated with different kinds of medicines. However, since these products are manufactured by coating and laminating on upper and lower portions thereof, the thickness of the film is thickened, and thus, the film is not well dried. Therefore, there is a problem in that the productivity is lowered and it is difficult to ensure product quality.

In addition, the products where different kinds of medicines are coated and laminated are disadvantageous in that it is impossible to separately take the medicines in a situation where separate taking is required.

DISCLOSURE

Technical Problem

The present invention is to provide an apparatus and method of manufacturing a multi-column multi-medicine oral dissolving film according to the present invention, where all processes from film feeding, medicine coating, and medicine drying to product packaging are implemented as continuous automation processes, and under the automation processes, different kinds of medicines are coated on a base film in multiple columns in a signal layer by using a plurality of nozzles supplied with the different kinds of medicines, so that it is possible to improve productivity through the automation processes, to ensure product quality due to efficiency during drying caused by maintaining the thickness of the product, and to provide a convenience in the case of taking various kinds of small-amount medicines at one time or in the case of separately and selectively taking different kinds of medicines.

Technical Solution

According to an aspect of the present invention, there is provided an apparatus for manufacturing a multi-column multi-medicine oral dissolving film, including a lower wrapping sheet feeding unit for feeding a lower wrapping sheet coated with the oral dissolving film and a lower wrapping sheet feeding unit for feeding the lower wrapping sheet coated with the oral dissolving film; an oral dissolving film coating unit for coating a raw solution of an oral dissolving film in a form of a film on an upper surface of the lower wrapping sheet fed from the lower wrapping sheet feeding unit; a drying unit for drying the oral dissolving film coated by the oral dissolving film coating unit by hot air, infrared rays, dehumidifying methods, and the like; an upper wrapping sheet feeding unit for feeding an upper wrapping sheet to an upper portion of the oral dissolving film which has been dried by the drying unit; a sealing unit for separately sealing the individual oral dissolving films by bonding the upper wrapping sheet and the lower wrapping sheet to a periphery of each of the oral dissolving films by a thermocompression bonding method; and a pouch packaging unit for separating the oral dissolving films separately sealed by the sealing unit into individual products by printing, slitting, and cutting the oral dissolving films.

In particular, the oral dissolving film coating unit of the apparatus for manufacturing a multi-column multi-medicine oral dissolving film includes a second medicine supply nozzle and a first medicine supply nozzle which are arranged at the upper and lower sides with a plurality of nozzle holes which are arranged at a certain interval, and the second medicine supply nozzle and the first medicine supply nozzle are coated in multiple columns so as to connected continuously with each other without being overlapped.

Herein, different medicines coated by the second medicine supply nozzle and the first medicine supply nozzle are coated in such a form that second medicines coated by the second medicine supply nozzle are arranged side by side in a row to be connected continuously with first medicines coated by the first medicine supply nozzle.

In addition, each of the second medicine supply nozzle and the first medicine supply nozzle may include a nozzle base which is movable forward and backward along a guide rail on a frame, a nozzle body which is supported on the nozzle base in a structure rotatable about a pin and a a plurality of nozzle holes at a distal end thereof, a tilting cylinder which is arranged on the nozzle base to move the nozzle body, and a servo motor which is arranged on the frame to move the nozzle base forward and backward.

The apparatus for manufacturing a multi-column multi-medicine oral dissolving film may further include an upper conveying roller and a lower conveying roller which are arranged in front of the second medicine supply nozzle and the first medicine supply nozzle to guide advancing of the lower wrapping sheet and to support the lower wrapping sheet during the coating of the oral dissolving film.

According to another aspect, there is provided an apparatus for manufacturing a multi-column multi-medicine oral dissolving film, including: a lower wrapping sheet feeding unit for feeding a lower wrapping sheet where an excipient and a main material are coated in a form of a film; an excipient coating unit for coating the excipient on an upper surface of the lower wrapping sheet fed from the lower wrapping sheet feeding unit; a hot air drying unit for drying the excipient coated by the excipient coating unit by a hot air method; a main material coating unit for coating a main material in a form of a film on the excipient dried by the hot air drying unit; a natural wind drying unit for drying the main material coated by the main material coating unit by natural wind; an upper wrapping sheet feeding unit for feeding an upper wrapping sheet on an upper portion of an main material film dried by the natural wind drying unit; a sealing unit for separately sealing the individual main material films by bonding the upper wrapping sheet and the lower wrapping sheet to a periphery of each of the main material films by a thermocompression bonding method; and a pouch packaging unit for separating the main material films separately sealed by the sealing unit into individual products by printing, slitting, and cutting the main material films.

In addition, according to still another aspect of the present invention, there is provided a method of manufacturing a multi-column multi-medicine oral dissolving film including: a lower wrapping sheet feeding step of feeding a lower wrapping sheet coated with the oral dissolving film; an oral dissolving film coating step of coating the oral solution film separated with a predetermined size by injecting a raw solution of the oral dissolving film on a upper surface of the lower wrapping sheet fed in the lower wrapping sheet feeding step and moved along a plurality of roll routes; a drying step of drying the oral dissolving film coated in the oral dissolving film coating step by hot air, infrared rays, and dehumidifying methods; an upper wrapping sheet feeding step of feeding an upper wrapping sheet to an upper portion of the oral dissolving film dried in the drying step; a sealing step of separately sealing the individual oral dissolving films by bonding the upper wrapping sheet and the lower wrapping sheet to a periphery of each of the oral dissolving films by a thermocompression bonding method; and a cutting step of separating the oral dissolving films separately sealed in the sealing step into individual products by slitting and cutting the oral dissolving films.

In particular, the oral dissolving film coating step may include a step of performing multi-column coating by using a plurality of nozzles which have a plurality of nozzle holes arranged at a certain interval and are arranged above and below to be supplied with different medicines so that different medicines are coated in multiple columns in a single layer so as to be connected continuously with each other without being overlapped.

Herein, in the oral dissolving film coating step, different medicines coated by a plurality of nozzles may be coated in such a form that second medicines coated by an upper side nozzle are arranged side by side in a row to be connected continuously with first medicines coated by a lower side nozzle.

In addition, in the oral dissolving film coating step, while injecting and stopping of the injecting of the raw solution of the oral dissolving film are repeatedly performed by a plurality of nozzles, the oral dissolving films with a certain size separated at a certain interval may be coated in parallel in a multi-column arrangement in one coating step.

The method may further include a vision inspecting step of checking whether the individual oral dissolving film coated on the lower wrapping sheet is defective by using a vision means before the sealing step. The method may further include, after the sealing step, a step of marking a defective oral dissolving film with a punching machine and a step of detecting the defective oral dissolving film with a sensor and removing the defective oral dissolving film.

Advantageous Effects

An apparatus and method of manufacturing the multi-column multi-medicine oral dissolving film according to the present invention have the following effects.

First, products where different medicines are coated in multiple columns in a single layer on a base film, namely, products where two or more kinds of medicines are coated in multiple columns in a single layer to be connected continuously with each other without being overlapped with each other are implemented, it is possible to provide a convenience in the case of taking various kinds of small-amount medicines at one time or in the case of separately and selectively taking different kinds of medicines.

Second, since the film can be manufactured by a plurality of coating steps according to the medicine, it is possible to obtain effects in that the manufacturing process can be simplified and economical efficiency can be increased.

BEST MODE

Hereinafter, the present invention will be described in detail with reference to the accompanying drawings.

A term "oral dissolving film" as used in the present invention is used as a concept including the same as or equivalent to an oral disintegrating film or an edible film, and in describing the present invention, these films are collectively referred as an oral dissolvable film.

Figure 1:
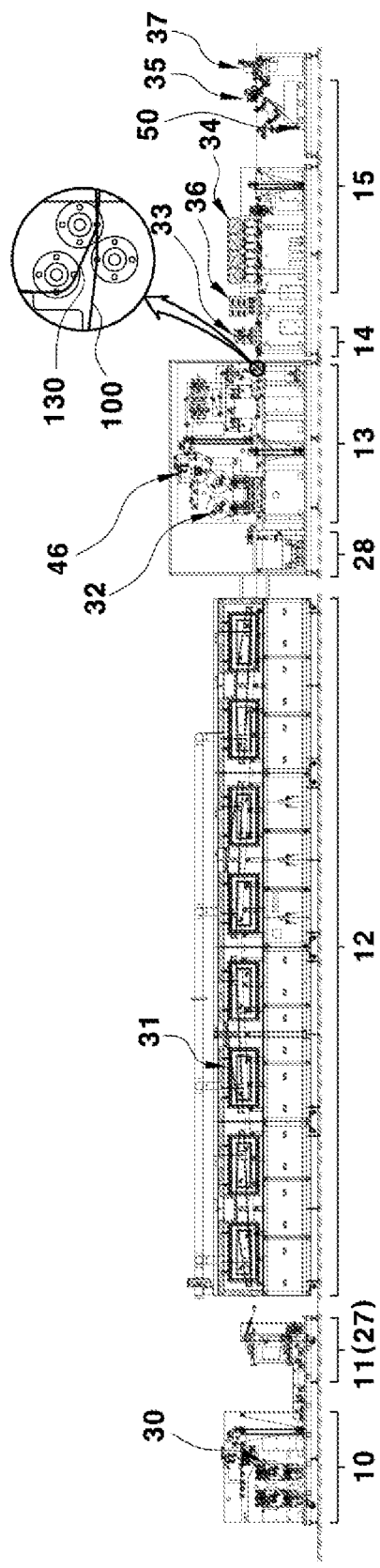
FIG. 1 is a front view illustrating an overall layout of an apparatus for manufacturing a multi-column multi-medicine oral dissolving film according to an embodiment of the present invention.

FIG. 1 is a front view illustrating the overall layout of an apparatus for manufacturing a multi-column multi-medicine oral dissolving film according to an embodiment of the present invention.

As illustrated in FIG. 1, the apparatus for manufacturing a multi-column multi-medicine oral dissolving film is configured to include a unit for feeding a lower wrapping sheet, a unit for coating the oral dissolving film on the lower wrapping sheet, a unit for drying the oral dissolving film by hot air, a unit for feeding the upper wrapping sheet, a unit for sealing the oral dissolving film with the upper and lower wrapping sheets, and a unit for separating the oral dissolving film into individual products and packaging the products, and the like.

In particular, in the portion where the oral dissolving film is coated, two injecting nozzles installed at the upper and lower sides at a certain interval perform a plurality of coating steps of coating the oral dissolving films having the same size, namely, a raw solution of an oral dissolving film on the inner surface (upper surface) of the lower wrapping sheet so as to be connected without being overlapped, so that it is possible to coat the oral dissolving films of different medicines in multiple columns in a single layer.

For this reason, the apparatus for manufacturing a multi-column multi-medicine oral dissolving film is configured to further include a lower wrapping sheet feeding unit 10 for feeding a lower wrapping sheet serving as a base on which the oral dissolving film is coated.

The lower wrapping sheet feeding unit 10 is a means for continuously feeding the lower wrapping sheet wound in a roll form while advancing the lower wrapping sheet along a plurality of roll routes. The lower wrapping sheet feeding unit includes at least one to two lower wrapping sheet winding bobbins 30 to automatically and continuously feed the lower wrapping sheets.

Herein, it is preferable that the two lower wrapping sheet winding bobbins 30 separated from each other with certain spacing are provided in an alternately automatically switched manner so that the lower wrapping sheets can be continuously fed.

The lower wrapping sheet fed from the lower wrapping sheet feeding unit 10 is allowed to enter the lower region of the oral dissolving film coating unit 11.

In addition, the apparatus for manufacturing a multi-column multi-medicine oral dissolving film is configured to further include an oral dissolving film coating unit 11 for coating different medicines in a single layer in parallel on an inner surface of the lower wrapping sheet fed from the lower wrapping sheet feeding unit 10.

The oral dissolving film coating unit 11 is a means which coats the oral dissolving films in multiple columns in parallel so as to be connected to each other without being overlapped by using a plurality of nozzles having a plurality of nozzle holes (reference numeral 16 in FIGS. 2 and 3) in order to be connected so as to be connected.

Namely, the oral dissolving film coating unit 11 can coat a raw solution of the oral dissolving film in a form of a film on the upper surface of the lower wrapping sheet fed from the lower wrapping sheet feeding unit 10 and can coat a raw solution of a different oral dissolving film so as not to be overlapped, namely, so as to be connected in a single layer.

The oral dissolving film coating unit 11 are connected continuously with the rear end of the lower wrapping sheet feeding unit 10, and after the completion of the coating in the oral dissolving film coating unit 11, the oral dissolving film and the lower wrapping sheet can be transferred to a drying unit 12.

In addition, the apparatus for manufacturing a multi-column multi-medicine oral dissolving film is configured to further include the drying unit 12 for drying the oral dissolving film coated by the oral dissolving film coating unit (11) by hot air, infrared rays, a dehumidifying method, or the like.

The drying unit 12 is a means for drying the oral dissolving film at a temperature of 30 to 130° C. The driving unit includes a plurality of dryers 31 arranged in a row, and while the lower wrapping sheet coated with the oral dissolving film is advanced along a plurality of rolls provided inside the dryer 31, the oral dissolving film can be dried.

In addition, the apparatus for manufacturing a multi-column multi-medicine oral dissolving film is configured to further include an upper wrapping sheet feeding unit 13 for feeding an upper wrapping sheet to an upper portion of the oral dissolving film dried by a drying unit (12).

The upper wrapping sheet feeding unit 13 is a means for feeding the upper wrapping sheet for wrapping the oral dissolving film, namely, the dried oral dissolving film coated on the upper surface of the lower wrapping sheet. The upper wrapping sheet feeding unit includes at least one to two lower wrapping sheet winding bobbins 30 to automatically and continuously feed the upper wrapping sheets 130.

Herein, it is preferable that the two upper wrapping sheet winding bobbins 32 separated from each other with certain spacing are provided in an alternately automatically switched manner so that the lower wrapping sheets can be continuously fed.

The upper wrapping sheet feeding unit 13 is arranged on the upper side of the rear end of the drying unit 12, and the upper wrapping sheet fed from the upper wrapping sheet feeding unit 13 is allowed to enter a sealing area of a sealing unit 14.

Namely, the upper wrapping sheet fed by an automatic transport system in accordance with the size of the lower wrapping sheet is allowed to enter a working area of the sealing machine 33 of the sealing unit 14 in a state where the upper wrapping sheet is combined with the upper portion of the lower wrapping sheet by an injector.

In addition, the apparatus for manufacturing a multi-column multi-medicine oral dissolving film is configured to further include the sealing unit 14 for separately sealing the individual oral dissolving films by bonding the upper wrapping sheet and the lower wrapping sheet to the periphery of the oral dissolving film by a thermocompression bonding method.

The sealing unit 14 is a means for separately sealing the individual oral dissolving films into individual packages by bonding the upper and lower wrapping sheet to the periphery of each oral dissolving film between the upper wrapping sheet and the lower wrapping sheet by a thermocompression bonding method. The sealing unit is provided with a sealing machine 33.

In addition, the apparatus for manufacturing a multi-column multi-medicine oral dissolving film is configured to further include a pouch packaging unit 15 for slitting and cutting each oral dissolving film separately sealed by the sealing unit 14 into individual products.

The pouch packaging unit 15 includes a lot print unit 34, a slitter 35, and a cutter 37. The lot print unit 34 is configured to print product information on the upper and lower wrapping sheets by using an inkjet printer. The slitter 35 performs a slitting operation in the direction of travel (the length direction of the wrapping sheet) of the product sealed in multiple columns in the parallel direction, namely, the wrapped product. The cutter 37 performs a cutting operation in the transverse direction (wrapping sheet width direction).

The apparatus for manufacturing a multi-column multi-medicine oral dissolving film is configured to further include a vision inspecting unit 46 arranged between the rear end of the upper wrapping sheet winding bobbin 32 and the front end of the sealing unit 14.

Herein, the vision inspecting unit 46 serves to check whether or not the oral dissolving film before being separately sealed in the sealing step is defective by using a vision camera.

In other words, the vision inspecting unit 46 serves to inspect whether or not contaminating substances are mixed into the oral dissolving film, coating failure of the oral dissolving film occurs, or the oral dissolving film is missing.

The sealing unit 14 is provided with a defect marking punching machine 36 for marking defects according to a result of the vision inspecting unit and punching the defective product. Therefore, the sealing unit can further perform a defect marking step.

In particular, in the pouch packaging unit 15, after the product information is printed by the ink jet printer, before the packaging, the defective product is detected, and the oral dissolving film which is marked (punched) by the sealing unit 14 as defective is detected by the defect detection sensor 50. Therefore, the defective products can be easily removed by the cutter 37.

The detailed structures and operating methods of the lower wrapping sheet feeding unit, the drying unit, the upper wrapping sheet feeding unit, the vision inspecting unit, the sealing unit, and the pouch packaging unit according to the present invention are the same as those of an apparatus for manufacturing an oral dissolving film in the related art, and thus, detail description thereof will be omitted.

On the other hand, in the present invention, in the case of separately coating an excipient (an agent for giving a proper size or shape to a liquid) and a main material, a method of separately coating and driving the the excipient and the main material is used.

For this reason, an excipient coating unit 27 for coating the excipient on the upper surface of the lower wrapping sheet is provided at the rear end of the lower wrapping sheet feeding unit 10 for feeding the lower wrapping sheet coated with the excipient and the main material in a form of a film.

In this case, the excipient coating unit 27 can coat the excipient on the upper surface of the lower wrapping sheet by using a nozzle means or the like in the oral dissolving film coating unit 11.

A drying unit 12 for drying the excipient coated with the excipient coating unit 27 by hot air, infrared rays, or a dehumidifying method is arranged at the rear end of the excipient coating unit 27. In the drying unit 12, the excipient can be dried in such a manner that the excipient on the lower wrapping sheet is injected with hot air in a temperature of 30 to 130° C.

In particular, a main material coating unit 28 is arranged at the rear end of the drying unit 12. The main material coating unit 28 serves to coat the main material on the excipient dried by the drying unit 12 in a form of a film.

Figure 4:
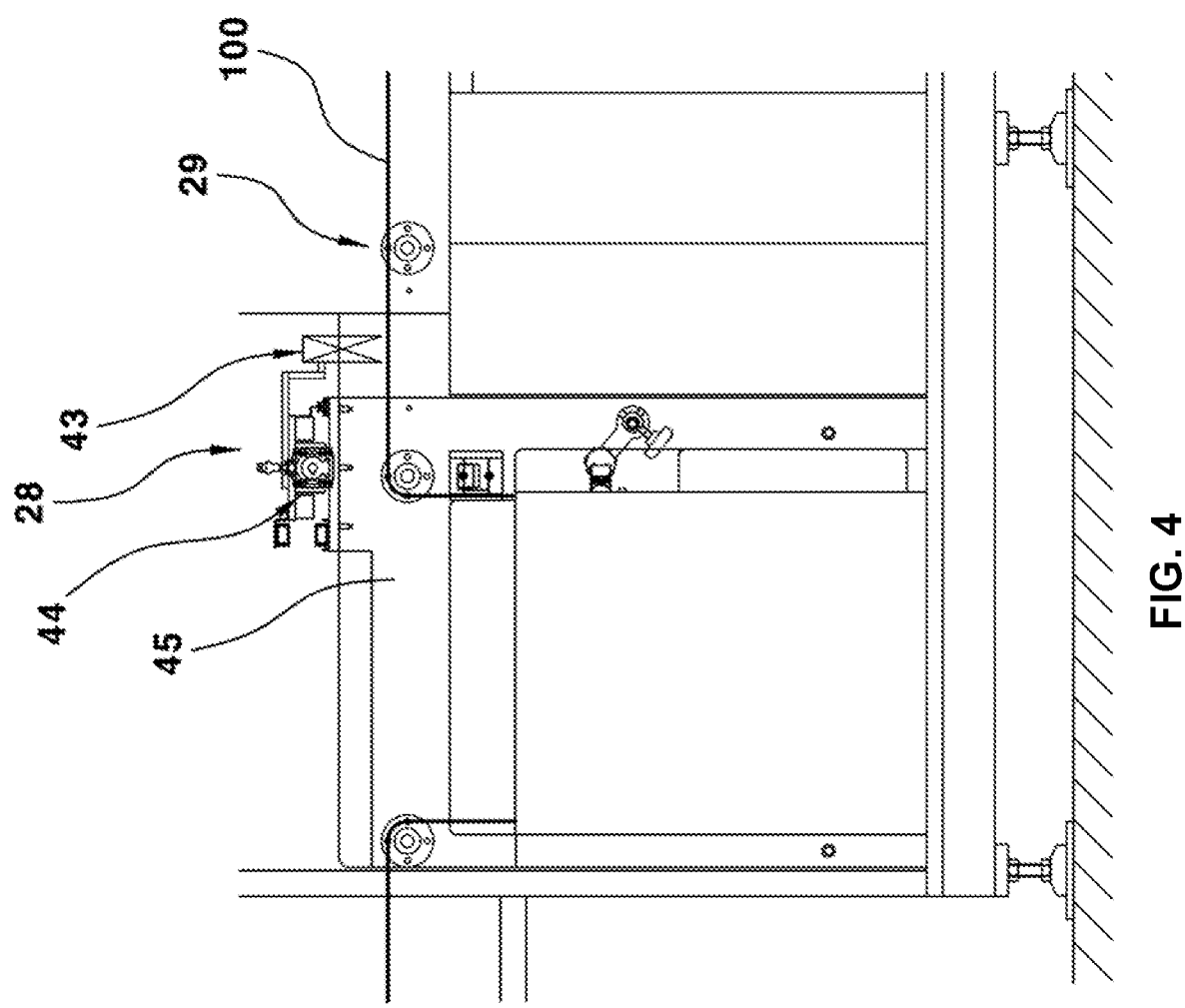
FIG. 4 is a front view illustrating a main material coating unit of an apparatus for manufacturing a multi-column multi-medicine oral dissolving film according to an embodiment of the present invention.

Herein, as illustrated in FIG. 4, the main material coating unit 28 is provided with a main material coating nozzle 43 for coating the main material with dispensing, inkjet printing, and powder spraying methods. The main material coating nozzle 43 is installed in a structure capable of separately injecting (dispensing, inkjet printing, and powder spraying) on an auxiliary frame 45 arranged at the rear stage of the main material coating unit 28.

Therefore, when the lower wrapping sheet coated with the excipient dried by the drying unit 12 enters a main material coating area, a main material is coated on the excipient in an individual injecting (dispensing, inkjet printing, and powder spraying) method by using the main material coating nozzle 43 positioned at the upper portion. Subsequently, the lower wrapping sheet is advanced to the side of a natural wind/dehumidifying drying unit 29, and after that, the post processes such as vision, sealing, punching, slitting, and cutting can be performed.

In addition, a natural wind/dehumidifying drying unit 29 for drying the main material coated by the main material coating unit 28 by natural wind or dehumidification is arranged at the rear end of the main material coating unit 28. The natural wind/dehumidifying drying unit 29 can dry the main material by injecting the natural wind having a room temperature (15 to 25° C.) or by performing as it is under the room temperature condition. The natural wind/dehumidifying drying unit 29 may be provided with a blowing fan to speedily perform the drying at the room temperature, so that it is possible to reduce the drying time.

An upper wrapping sheet feeding unit 13 for feeding an upper wrapping sheet to an upper portion of the main material film dried by the natural wind/dehumidifying drying unit 29, a sealing unit 14 for separately sealing the main material film by bonding the upper wrapping sheet and the lower wrapping sheet to a periphery of each of the individual main material films by a thermocompression bonding method, a pouch packaging unit 15 for separating he main material film separately sealed by the sealing unity 14 into individual products by slitting and cutting the main material film, and the like are sequentially arranged at the rear end of the natural wind/dehumidifying drying unit 29, so that each step can be performed.

In this manner, by primarily coating and drying the excipient, secondarily coating the main material which is generally vulnerable to heat, and drying by natural wind and dehumidification, it is possible to efficiently coat the main material which may be damaged by heat.

Figure 2A:
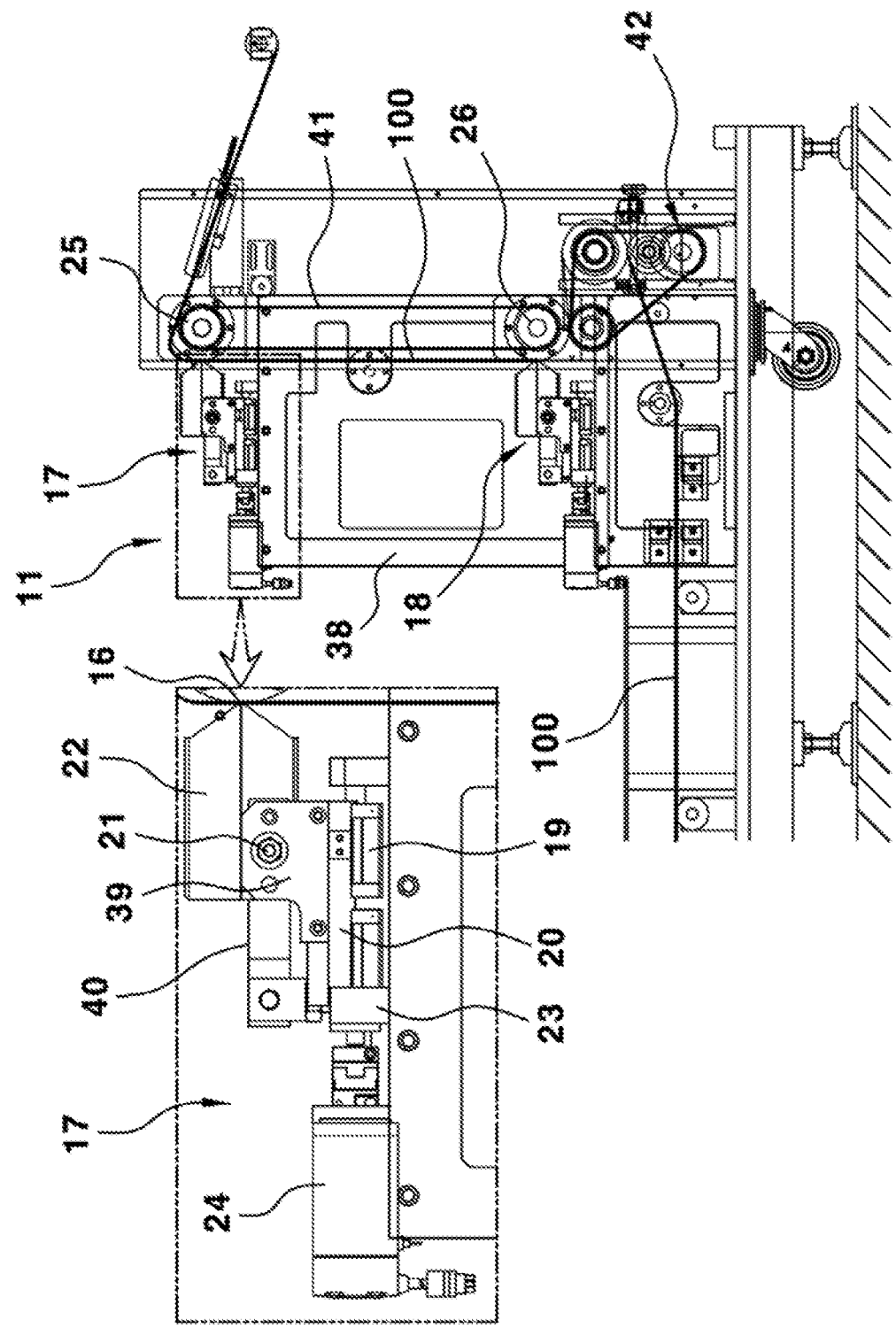
FIGS. 2a and 2b are a front view and a plan view illustrating a single-layered multi-column heterogeneous-medicine coating unit of the apparatus for manufacturing multi-column multi-medicine oral dissolving films according to the embodiment of the present invention.
Figure 2B:
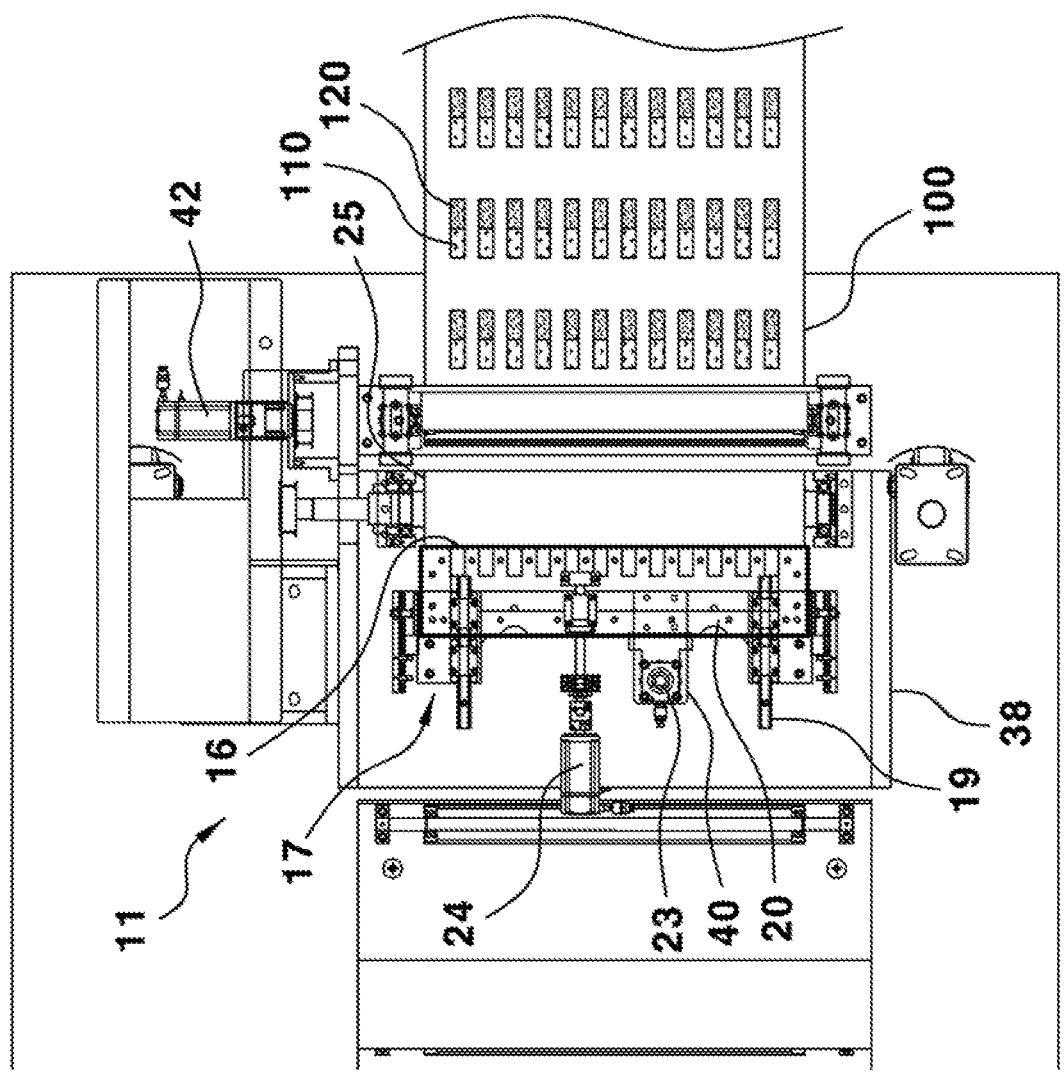

FIGS. 2a and 2b are a front view and a plan view illustrating a single-layered multi-column heterogeneous-medicine coating unit of the apparatus for manufacturing multi-column multi-medicine oral dissolving films according to the embodiment of the present invention.

As illustrated in FIGS. 2a and 2b, the oral dissolving film coating unit 11 sequentially coats different medicines in multiple columns in a single layer side by side so that the different kinds of medicines are not overlapped.

For this reason, a second medicine supply nozzle 17 and a first medicine supply nozzle 18 are arranged at a predetermined distance from each other on the upper and lower portions of a frame 38 of the apparatus, respectively. The second and first medicine supply nozzles 17 and 18 arranged in this manner coat the different kinds of medicines on the inner surface of the lower wrapping sheet by the forward and backward movements and the rotational movement.

A plurality of nozzle holes 16 arranged at a certain interval along the left and right direction of the nozzles are formed at the distal ends of the second and first medicine supply nozzles 17 and 18. The medicines are intermittently ejected through the nozzle holes 16 at this time, so that the oral dissolving films are simultaneously coated on the lower wrapping sheet in multiple columns in parallel.

Herein, the plurality of nozzle holes 16 of the second medicine supply nozzle 17 and the plurality of nozzle holes 16 of the first medicine supply nozzle 18 are arranged so as to be arranged at the same pitch and located at the same place above and below.

Accordingly, the oral dissolving film medicine ejected from the nozzle holes 16 of the second medicine supply nozzle 17 and the oral dissolving film medicine ejected from the nozzle holes of the first medicine supply nozzle 18 are coated on the same line on the lower wrapping sheet.

Of course, medicine supply containers (not shown) storing different kinds of medicines are connected to the second medicine supply nozzle 17 and the first medicine supply nozzle 18, respectively, and the nozzles cab eject different medicines to coat the different medicines on the lower wrapping sheet.

For the forward and backward movement and rotational movement of the second and first medicine supply nozzles 17 and 18, guide rails 19 are provided on both sides of the frame 28. A nozzle base 20 serving as a nozzle support is installed on the guide rails 19 installed in this manner.

Accordingly, the nozzle base 20 can move forward and backward along the guide rails 19, so that the nozzles supported on the nozzle base 20 can move forward and backward together with the nozzle base.

Support plates 39 are provided on both side surface portions of the nozzle base 20. The nozzles are arranged between the nozzle plates 39, and the side surface portions of the nozzles are engaged with a pin 21, so that the second medicine supply nozzle 17 and the first medicine supply nozzle 18 can rotate up and down about a pin 21 as an axis.

A tilting cylinder 23 is provided as a drive source for rotating operation of the second and first medicine supply nozzles 17 and 18. The tilting cylinder 23 is supported in a vertical posture on the rear surface of the nozzle base 20. The rod thereof is connected to a connector bracket 40 attached to the rear surface of the second and first medicine supply nozzles 17 and 18.

Accordingly, when the tilting cylinder 23 moves backward (rod being lifted down), the second and first medicine supply nozzles 17 and 18 rotate around the pin 21, and thus, the distal end thereof is lifted upward, so that the nozzles can be separated from the lower wrapping sheet side.

Similarly, when the tilting cylinder 23 moves forward (rod being lifted up), the second and first medicine supply nozzles 17 and 18 rotate around the pin 21, so that the nozzles can return to an initial horizontal posture.

A servomotor 24 for forward and backward movements is provided as a driving source for the forward and backward movements of the second and first medicine supply nozzles 17 and 18. The servomotor 24 for forward and backward movements is provided on the frame 38, and the rod thereof is connected to the rear portion of the nozzle base 20 through a coupling or the like.

Accordingly, through the forward and backward movements by the servomotor 24 for forward and backward movements, all the second and first medicine supply nozzles 17 and 18 including the nozzle base 20 can be moved forward and backward. Due to these movements, the second and first medicine supply nozzles 17 and 18 are allowed to come out of the backward position after coating the oral dissolving film while being close to the lower wrapping sheet side at the forward position.

Figure 3:
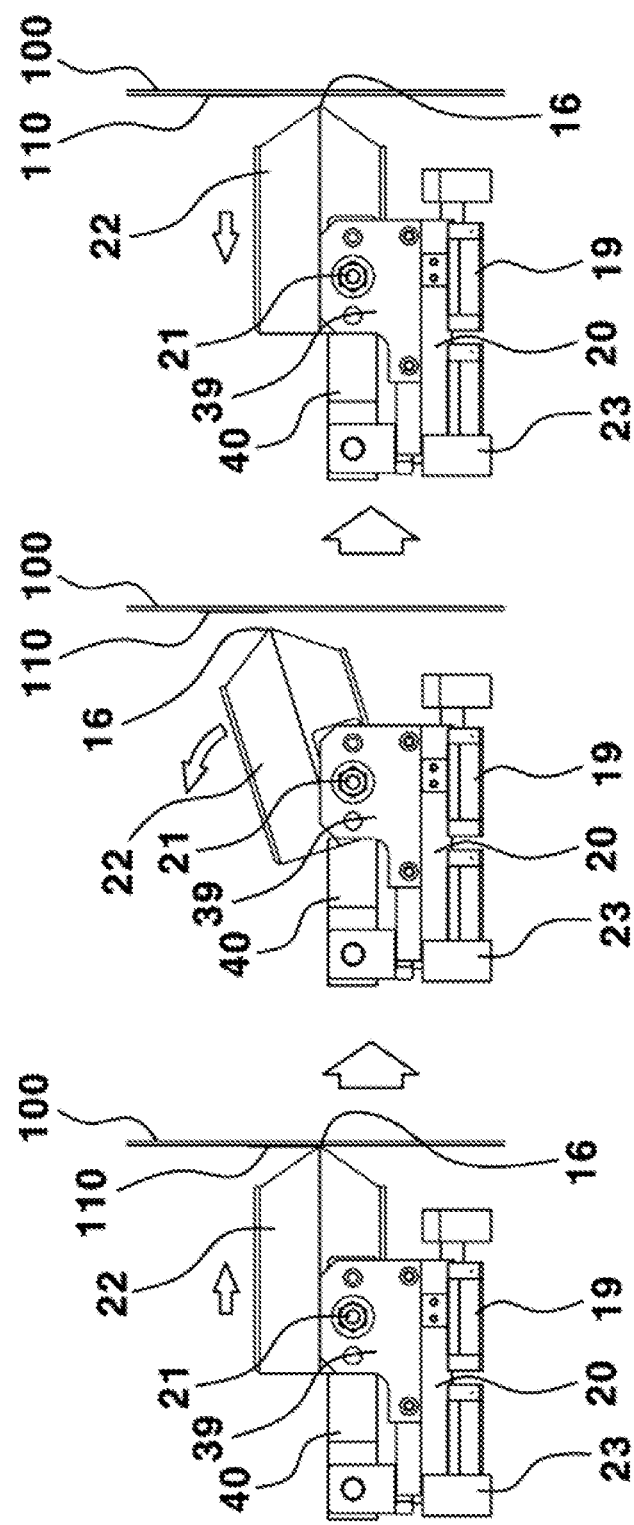
FIG. 3 is a front view illustrating a state of a coating operation of the single-layered multi-column heterogeneous-medicine coating unit of the apparatus for manufacturing multi-column multi-medicine oral dissolving films according to the embodiment of the present invention.

For example, as illustrated in FIG. 3, the second and first medicine supply nozzles 17 and 18 can continuously coat the oral dissolving film on the lower wrapping sheet at a certain pitch interval in the wrapping sheet advancing direction while repeating the operations of forward movement->coating (medicine injecting)->lifting up (medicine injecting stop)->backward movement->returning.

In addition, two conveying rollers, namely, an upper conveying roller 25 and a lower conveying roller 26 are used as means for supporting the lower wrapping sheet while the coating step by the second and first medicine supply nozzles 17 and 18 is performed.

The upper conveying roller 25 and the lower conveying roller 26 are supported at both ends of the frame 38 while being arranged side by side in front of the second and first medicine supply nozzles 17 and 18. The upper and lower conveying rollers are allowed to rotate by a motor 42 to serve to guide the advancing of the lower wrapping sheet and to support an outer side surface of the lower wrapping sheet during the coating.

Herein, the upper conveying roller 25 and the lower conveying roller 26 are connected by a belt 41, so that the rollers can rotate simultaneously in the same direction.

Accordingly, in a state where the lower wrapping sheet 100 fed from the lower wrapping sheet feeding unit 10 advances through the lower conveying roller 26 and the upper conveying roller 25 in this order, the inner surface of the lower wrapping sheet 100 is primarily coated with a first medicines 110 in multiple columns by the operation of the first medicine supply nozzle 18. Subsequently, the lower wrapping sheet 100 coated with the first medicines 110 is advanced to the upper portion, and the inner surface of the lower wrapping sheet 100 is secondarily coated with a second medicines 120 of which kind is different from that of the first medicines 110 in multiple columns by the operation of the second medicine supply nozzle 17.

In particular, the second medicines 120 and the first medicines 110 which are coated by the second medicine supply nozzle 17 and the first medicine supply nozzle 18 are coated so as to be connected continuously with each other in a single layer without being overlapped. For example, the first medicines 110 coated by the first medicine supply nozzle 18 and the second medicines 120 coated by the second medicine supply nozzle 17 may be coated in such a form that the second medicines are arranged side by side in a row in the wrapping sheet advancing direction to be connected continuously with the first medicines.

For example, the second medicines 120 coated by the second medicine supply nozzle 17 may be connected continuously with the front side of the first medicines 110 coated by the first medicine supply nozzle 18.

In this manner, the different medicines are coated in multiple columns in a single layer by using the second medicine supply nozzle 17 and the first medicine supply nozzle 18, so that there is no burden to take medicines in the case of taking various medicines at the same time, and it is easy to take medicines in the case of separately taking the medicines. In particular, since the different kinds of medicines are coated in a single layer, the thickness can be reduced, so that the efficiency of the process can be secured, for example, the drying step can be effectively performed.

Figure 5:
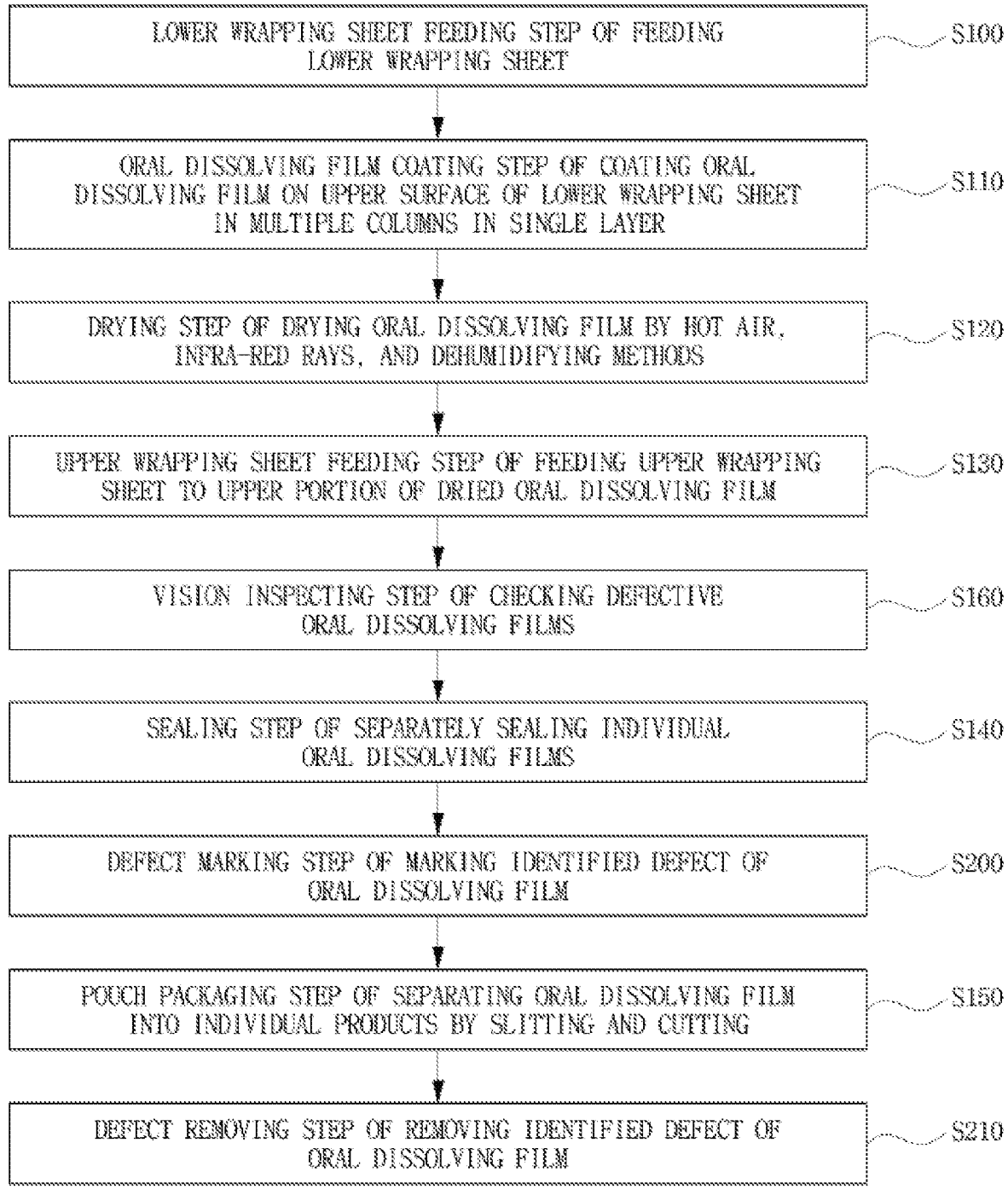
FIG. 5 is a block diagram illustrating a method of manufacturing a multi-column multi-medicine oral dissolving film according to an embodiment of the present invention.

FIG. 5 is a block diagram illustrating a method of manufacturing a multi-column multi-medicine oral dissolving film according to an embodiment of the present invention.

As illustrated in FIG. 5, the method of manufacturing a multi-column multi-medicine oral dissolving film includes, as basic steps, a lower wrapping sheet feeding step S100, an oral dissolving film coating step S110, a drying step S120, an upper wrapping sheet feeding step S130, a sealing step S140, a defect marking step S200, a pouch packaging step S150, a defect removing step S210, and the like.

In addition, the method may further include a vision inspecting step S160 of checking whether or not each oral dissolving film sealed separately is defective by using a vision means between the upper wrapping sheet feeding step S130 and the sealing step S140.

Herein, the lower wrapping sheet feeding step S100 is a step of feeding the lower wrapping sheet coated with the oral dissolving film. The drying step S120 is a step of drying the oral dissolving film which has been coated by hot air, infrared rays and dehumidifying. The upper wrapping sheet feeding step S130 is a step of feeding the upper wrapping sheet to the upper portion of the dried oral dissolving film. The vision inspecting step S160 is a step of inspecting a state of the oral dissolving film coated on the lower wrapping sheet. The sealing step S140 is a step of separately sealing the individual oral dissolving films by bonding the upper wrapping sheet and the lower wrapping sheet to the periphery of each of the oral dissolving films where different medicines are arranged in multiple columns in a single layer by a thermocompression bonding method. The defect marking step S200 is a step of marking the defective oral dissolving film checked by the vision inspecting unit with a defect marking punching machine 36. The pouch packaging step S150 is a step of slitting and cutting each of separately sealed oral dissolving films into individual products. The defect removing step S210 is a step of removing individual defective oral dissolving films detected by a defect detection sensor 50. In this case, the lower wrapping sheet feeding step S100, the drying step S120, the upper wrapping sheet feeding step S130, the vision inspecting step S160, the sealing step S140, and the pouch packaging step S150 are the same as those in the related art, and thus, the detailed description thereof will be omitted.

In particular, the oral dissolving film coating step S110 is a step of coating the oral dissolving films separated with a predetermined size in multiple columns in a single layer by injecting the raw solution of the oral dissolving film on the upper surface of the lower wrapping sheet fed and moved in the lower wrapping sheet feeding step S100.

In these oral dissolving film coating steps, injecting and stopping of the injecting of the raw solution of the oral dissolving film are repeatedly performed by a plurality of nozzles having a large number of nozzle holes, and by performing the coating step once through the nozzles, the oral dissolving films with a certain size separated at a certain interval are coated in parallel in multiple columns.

In particular, in the oral dissolving film coating step, by using the second medicine supply nozzle and the first medicine supply nozzle which are arranged in the upper and lower portions with a predetermined height difference and supplied with different medicines, different medicines can be coated on the oral dissolving film in multiple columns in a single layer to be connected continuously with each other without being overlapped with each other For example, the oral dissolving film can be coated with different medicines by respective nozzles. Namely, the oral dissolving film can be coated in a form that the first medicine and the second medicine are arranged side by side in a row, that is, in a form that the second medicine is arranged side by side in a raw to connected continuously with the first medicine in front of the first medicine coated by the lower nozzle.

Figure 6:
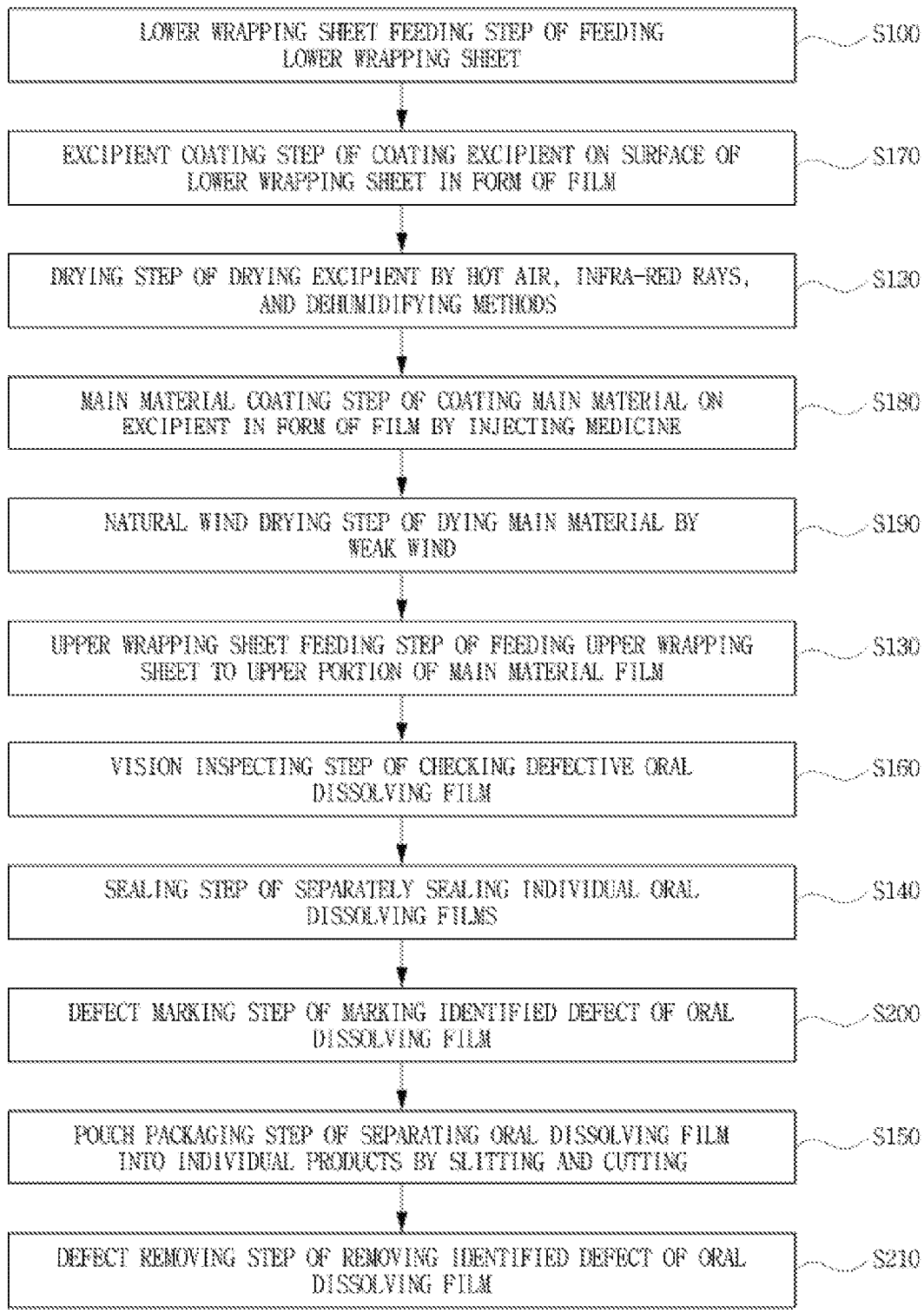
FIG. 6 is a block diagram illustrating a method of manufacturing a multi-column multi-medicine oral dissolving film according to another embodiment of the present invention.

FIG. 6 is a block diagram illustrating a method of manufacturing a multi-column multi-medicine oral dissolving film according to another embodiment of the present invention.

As illustrated in FIG. 6, the method of manufacturing a multi-column multi-medicine oral dissolving film includes, as basic steps, a lower wrapping sheet feeding step S100, an excipient coating step S170, a hot air drying step S120, a main material coating step S180, a natural wind drying step S190, an upper wrapping sheet feeding step S130, a vision inspecting step S160, a sealing step S140, a defect marking step S200, a pouch packaging step S150, and a defect removing step S210.

Herein, the lower wrapping sheet feeding step S100 is a step of feeding the lower wrapping sheet coated with the oral dissolving film. The drying step S120 is a step of drying the coated oral dissolving film by hot air, infrared rays, and dehumidifying methods. The upper wrapping sheet feeding step is a step of feeding the upper wrapping sheet to the upper portion of the dried oral dissolving film. The sealing step S140 is a step of separately sealing the individual oral dissolving films by bonding the upper wrapping sheet and the lower wrapping sheet to the periphery of each of the oral dissolving films where different medicines are arranged in multiple columns in a single layer by a thermocompression bonding method. The cutting step S150 is a step of slitting and cutting each of separately sealed oral dissolving films into individual products. In this case, the lower wrapping sheet feeding step S100, the hot air drying step S120, the upper wrapping sheet feeding step S130, the vision inspecting step S160, the sealing step S140, and the pouch packaging step S150 are the same as those in the related art, and thus, the detailed description thereof will be omitted.

In particular, the excipient coating step S170 and the main material coating step S180 can be performed as separate coating steps, and the coated excipient and the main material can also be dried under a drying condition or under individual drying conditions.

In the excipient coating step, the excipients separated with a predetermined size are coated in a form of a film by injecting the excipient on the upper surface of the lower wrapping sheet which is fed and moved in the lower wrapping sheet feeding step by the nozzle means.

Subsequently, in the excipient coating step, the coated excipient is dried at a temperature of 30 to 130° C. while being dried by hot air, infrared ray, dehumidifying method, or the like.

In the main material coating step, the main material is separately injected on the excipient dried in the drying step by a nozzle means such as dispensing, inkjet printing, and powder spraying methods, so that the main material is coated in a form of a film.

Subsequently, the main material coated in the main material coating step is dried by a natural wind or dehumidification under a temperature condition of a room temperature (15 to 25° C.).

As described above, in the step of separately coating the excipient and the main material during the medicine coating, the excipient is primarily coated and dried by hot air, infrared ray, and dehumidifying method. After that, the main material which is vulnerable to heat is secondarily coated and dried by natural drying. As a result, it is possible to prevent occurrence of defects such as damage of main material and to ensure product quality.

INDUSTRIAL AVAILABILITY

In the present invention, the entire processes from the oral dissolving film coating to the final packaging are performed as continuous automation processes in the same production line to produce separated products, so that productivity can be improved. On the other hand, by providing products where different medicines (different kinds of medicines) are coated in multiple columns in a single layer, it is possible to take the medicines conveniently in the case of taking many medicines at once or in the case of separately taking medicines.

What is claimed is:

1. An apparatus for manufacturing a multi-column multi-medicine oral dissolving film comprising an oral dissolving film coating unit for coating a raw solution of the oral dissolving film in a form of a film,
   wherein the oral dissolving film coating unit includes:
   a first medicine supply nozzle which is connected to a first medicine container supplying a first medicine raw solution and ejects the first medicine to coat lower wrapping sheet in a form of a film; and
   a second medicine supply nozzle which is connected to a second medicine container which is arranged so as to be adjacent to the first medicine supply nozzle and supplies a second medicine raw solution which is different from the first medicine and ejects the second medicine to coat the lower wrapping sheet in a form of a film, and
   wherein the different medicines are coated in multiple columns on the lower wrapping sheet so as to be connected continuously with each other in a single layer without being overlapped.

2. The apparatus according to claim 1, wherein the first medicine supply nozzle and the second medicine supply nozzle are provided with each of a plurality of nozzle holes which are arranged at a certain interval.

3. The apparatus according to claim 1, wherein different medicines coated by the second medicine supply nozzle and the first medicine supply nozzle are coated in such a form that second medicines coated by the second medicine supply nozzle are arranged side by side in a row to be connected continuously with first medicines coated by the first medicine supply nozzle.

4. The apparatus according to claim 1, further comprising:
   a lower wrapping sheet feeding unit which is arranged in front of the oral dissolving film coating unit and feeds the lower wrapping sheet coated with the oral dissolving film to the oral dissolving film coating unit;
   a drying unit which is arranged immediately behind the oral dissolving film coating unit and dries the oral dissolving film coated by the oral dissolving film coating unit by hot air, infrared rays, and dehumidifying methods;
   an upper wrapping sheet feeding unit which feeds an upper wrapping sheet to a top of the oral dissolving film dried by the hot air drying unit;
   a sealing unit which separately seals the oral dissolving film by bonding the upper wrapping sheet and the lower wrapping sheet to a periphery of each of the oral dissolving films by a thermocompression bonding method; and
   a pouch packaging unit which separates the oral dissolving films separately sealed by the sealing unit into individual products by slitting and cutting the oral dissolving films.

5. The apparatus according to claim 1,
   wherein each of the second medicine supply nozzle and the first medicine supply nozzle includes: a nozzle base which is movable forward and backward along a guide rail on a frame, a nozzle body which is supported on the nozzle base in a structure rotatable about a pin and has a plurality of nozzle holes at a distal end thereof; a tilting cylinder which is arranged on the nozzle base to move the nozzle body; and a servo motor which is arranged on the frame to move the nozzle base forward and backward, and
   wherein the medicine supply nozzles are arranged at upper and lower portions of the frame at predetermined intervals.

6. The apparatus according to claim 5, further comprising a second medicine supply nozzle and a lower conveying roller which are arranged in front of the second medicine supply nozzle and the first medicine supply nozzle to guide advancing of the lower wrapping sheet and to support the lower wrapping sheet during the coating of the oral dissolving film.

7. A method of manufacturing a multi-column multi-medicine oral dissolving film comprising:
   a lower wrapping sheet feeding step of feeding a lower wrapping sheet coated with the oral dissolving film;
   an oral dissolving film coating step of coating the oral solution film separated with a predetermined size by injecting a raw solution of the oral dissolving film on a upper surface of the lower wrapping sheet fed in the lower wrapping sheet feeding step and moved along a plurality of roll routes;
   a drying step of drying the oral dissolving film coated in the oral dissolving film coating step by hot air, infrared rays, and dehumidifying methods;
   an upper wrapping sheet feeding step of feeding an upper wrapping sheet to an upper portion of the oral dissolving film dried in the drying step;

a sealing step of separately sealing the oral dissolving film by bonding the upper wrapping sheet and the lower wrapping sheet to a periphery of each of the oral dissolving films by a thermocompression bonding method; and a pouch packaging step of separating the oral dissolving films separately sealed in the sealing step into individual products by slitting and cutting the oral dissolving films, wherein the oral dissolving film coating step includes a step of performing multi-column coating by using a plurality of nozzles which have a plurality of nozzle holes arranged at a certain interval and are arranged above and below to be supplied with different medicines so that different medicines are coated in multiple columns in a single layer so as to be connected continuously with each other without being overlapped.

8. The method according to claim 7, wherein, in the oral dissolving film coating step, different medicines coated by a plurality of nozzles are coated in such a form that second medicines coated by an upper side nozzle are arranged side by side in a row to be connected continuously with first medicines coated by a lower side nozzle.

9. The method according to claim 7, wherein, in the oral dissolving film coating step, while injecting and stopping of the injecting of the raw solution of the oral dissolving film are repeatedly performed by a plurality of nozzles, the oral dissolving films with a certain size separated at a certain interval are coated in parallel in a multi-column arrangement in one coating step.

10. The method according to claim 7, further comprising a vision inspecting step of checking whether the oral dissolving film coated on the lower wrapping sheet is defective by using a vision means before the sealing step.

11. The method of claim 10, further comprising:

a defect marking step of marking defects by punching a defective oral dissolving film by using a punching machine for marking defects after the sealing step; and a defect removing step of detecting the defective oral dissolving film by using a defect detection sensor after printing product information and removing the individual defective oral dissolving films after a cutting step.

* * * * *